United States Patent
Ruan et al.

(10) Patent No.: US 9,162,030 B2
(45) Date of Patent: Oct. 20, 2015

(54) SAFETY PEN NEEDLE ASSEMBLY HAVING SHIELDING FOR PATIENT AND NON-PATIENT ENDS

(71) Applicant: BECTON, DICKINSON AND COMPANY, Franklin Lakes, NJ (US)

(72) Inventors: Tieming Ruan, Randolph, NJ (US);
Stephen Richards, Holdrege, NE (US);
Eliot Zaiken, Covington, GA (US);
Craig Newman, Montvale, NJ (US);
Vadim Goykhman, Aventura, FL (US);
Joseph Alu, Oakland, NJ (US); Michael Vincent Quinn, East Hanover, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/134,810

(22) Filed: Dec. 19, 2013

(65) Prior Publication Data
US 2014/0107586 A1    Apr. 17, 2014

Related U.S. Application Data

(63) Continuation of application No. 12/922,802, filed as application No. PCT/UP2009/037084 on Mar. 13, 2009, now Pat. No. 8,632,503.

(60) Provisional application No. 61/036,138, filed on Mar. 13, 2008, provisional application No. 61/036,299, (Continued)

(51) Int. Cl.
*A61M 5/32* (2006.01)
*A61M 5/34* (2006.01)

(52) U.S. Cl.
CPC ............. *A61M 5/326* (2013.01); *A61M 5/3257* (2013.01); *A61M 5/347* (2013.01); *A61M 2005/3247* (2013.01); *A61M 2005/3254* (2013.01); *A61M 2005/3263* (2013.01)

(58) Field of Classification Search
CPC . A61M 5/3205; A61M 5/321; A61M 5/3213; A61M 5/322; A61M 5/3221; A61M 5/3228; A61M 5/3232; A61M 5/3234; A61M 5/3235; A61M 5/3236; A61M 5/3239; A61M 5/3243; A61M 5/3245; A61M 5/3246; A61M 5/3247; A61M 5/325; A61M 5/3252; A61M 5/3253; A61M 5/3254; A61M 2005/3228; A61M 2005/3235; A61M 2005/3236; A61M 2005/3239; A61M 2005/3246; A61M 2005/3247; A61M 2005/325; A61M 2005/3252; A61M 2005/3253; A61M 2005/3254; A61M 5/3257; A61M 5/326; A61M 5/347; A61M 2005/3263
USPC ......... 604/162, 163, 192, 193, 194, 195, 196, 604/197, 198
See application file for complete search history.

(56) References Cited

U.S. PATENT DOCUMENTS
4,894,055 A    1/1990 Sudnak
(Continued)

FOREIGN PATENT DOCUMENTS
DE       8909799 U1    11/1989
(Continued)

*Primary Examiner* — Bhisma Mehta
*Assistant Examiner* — Nicholas Meghri
(74) *Attorney, Agent, or Firm* — Dickinson Wright PLLC

(57) ABSTRACT

A safety pen needle assembly is provided herein which includes a hub and a needle fixed to the hub. Further, a first shield is provided, along with a second shield which has a biasing element disposed to urge the second shield proximally towards a proximal end of the needle. The assembly further includes a releasable retaining assembly for releasably retaining the second shield in an initial position against the force of the biasing element. A predetermined extent of movement of the first shield causes the retaining assembly to release the second shield. With the second shield being released, the second shield is urged proximally by the biasing element to a second position where the second shield covers the proximal end of the needle. Advantageously, an assembly is provided which allows for passive activation of a shield on a non-patient end of a pen needle assembly by a patient-end shield.

9 Claims, 15 Drawing Sheets

Related U.S. Application Data filed on Mar. 13, 2008, provisional application No. 61/055,686, filed on May 23, 2008, provisional application No. 61/081,878, filed on Jul. 18, 2008, provisional application No. 61/084,750, filed on Jul. 30, 2008.

(56) References Cited

U.S. PATENT DOCUMENTS

| | | |
|---|---|---|
| 4,897,083 A | 1/1990 | Martell |
| 4,921,491 A | 5/1990 | Champ |
| 4,998,924 A | 3/1991 | Ranford |
| 5,061,246 A | 10/1991 | Anapliotis |
| 5,193,552 A | 3/1993 | Columbus et al. |
| 5,246,428 A | 9/1993 | Falknor |
| 5,250,037 A | 10/1993 | Bitdinger |
| 5,256,153 A | 10/1993 | Hake |
| 5,269,765 A | 12/1993 | Kuracina |
| 5,279,579 A | 1/1994 | D'Amico |
| 5,292,314 A | 3/1994 | D'Alessio et al. |
| 5,336,197 A | 8/1994 | Kuracina et al. |
| 5,364,362 A | 11/1994 | Schulz |
| 5,389,085 A | 2/1995 | D'Alessio et al. |
| 5,417,662 A | 5/1995 | Hjertman et al. |
| 5,429,612 A | 7/1995 | Berthier |
| 5,514,097 A | 5/1996 | Knauer |
| 5,562,624 A | 10/1996 | Righi et al. |
| 5,591,138 A | 1/1997 | Vaillancourt |
| 5,609,577 A | 3/1997 | Haber et al. |
| 5,634,906 A | 6/1997 | Haber et al. |
| 5,688,241 A | 11/1997 | Asbaghi |
| 5,795,336 A | 8/1998 | Romano et al. |
| 5,810,775 A | 9/1998 | Shaw |
| 5,873,856 A | 2/1999 | Hjertman et al. |
| 5,964,739 A | 10/1999 | Champ |
| 5,971,966 A | 10/1999 | Lav |
| RE36,398 E | 11/1999 | Byrne et al. |
| 5,984,899 A | 11/1999 | D'Alessio et al. |
| RE36,447 E | 12/1999 | Byrne et al. |
| 6,017,329 A | 1/2000 | Hake |
| 6,110,147 A | 8/2000 | Perouse |
| 6,203,529 B1 | 3/2001 | Gabriel et al. |
| 6,224,576 B1 | 5/2001 | Thorne et al. |
| 6,379,336 B1 | 4/2002 | Asbaghi et al. |
| 6,547,764 B2 | 4/2003 | Larsen et al. |
| 6,569,124 B1 | 5/2003 | Perouse |
| 6,692,463 B1 | 2/2004 | Marteau et al. |
| 6,773,415 B2 | 8/2004 | Heiniger |
| 6,796,967 B2 | 9/2004 | Jensen |
| 6,855,129 B2 | 2/2005 | Jensen et al. |
| 6,939,330 B1 | 9/2005 | McConnell-Montalvo et al. |
| 6,986,760 B2 | 1/2006 | Giambattista et al. |
| 7,066,907 B2 | 6/2006 | Crossman et al. |
| 7,074,211 B1 | 7/2006 | Heiniger et al. |
| 7,147,624 B2 | 12/2006 | Hirsiger et al. |
| 7,198,617 B2 | 4/2007 | Millerd |
| 7,229,432 B2 | 6/2007 | Marshall et al. |
| 7,278,986 B1 | 10/2007 | Frost |
| 7,361,160 B2 | 4/2008 | Hommann et al. |
| 7,361,166 B2 | 4/2008 | Bosse et al. |
| 7,370,759 B2 | 5/2008 | Hommann |
| 7,374,558 B2 | 5/2008 | Kirchhofer |
| 7,384,414 B1 | 6/2008 | Marshall et al. |
| 7,442,185 B2 | 10/2008 | Amark et al. |
| 7,635,350 B2 | 12/2009 | Scherer |
| 8,177,745 B2 | 5/2012 | Brechbuehler et al. |
| 8,287,501 B2 | 10/2012 | Wei |
| 2002/0133122 A1 | 9/2002 | Giambattista et al. |
| 2002/0193746 A1 | 12/2002 | Chevallier |
| 2003/0014018 A1 | 1/2003 | Giambattista et al. |
| 2003/0120209 A1 | 6/2003 | Jensen et al. |
| 2004/0122379 A1 | 6/2004 | Bosse et al. |
| 2004/0193110 A1 | 9/2004 | Giambattista et al. |
| 2005/0113750 A1 | 5/2005 | Targell |
| 2005/0267410 A1 | 12/2005 | Koska |
| 2005/0277893 A1 | 12/2005 | Liversidge |
| 2005/0288607 A1 | 12/2005 | Konrad |
| 2006/0095010 A1 | 5/2006 | Westbye |
| 2006/0270984 A1 | 11/2006 | Hommann |
| 2007/0027430 A1 | 2/2007 | Hommann |
| 2007/0118081 A1 | 5/2007 | Daily et al. |
| 2007/0129674 A1 | 6/2007 | Liversidge |
| 2007/0156101 A1 | 7/2007 | Liversidge |
| 2007/0173772 A1 | 7/2007 | Liversidge |
| 2007/0255225 A1 | 11/2007 | Alchas et al. |
| 2008/0009807 A1 | 1/2008 | Hommann |
| 2008/0071225 A1 | 3/2008 | Hommann et al. |
| 2008/0077093 A1 | 3/2008 | Gratwohl et al. |
| 2008/0103453 A1 | 5/2008 | Liversidge |
| 2008/0103454 A1 | 5/2008 | Gratwohl et al. |
| 2008/0249477 A1 | 10/2008 | Paproski et al. |
| 2008/0255526 A1 | 10/2008 | Bosse et al. |
| 2008/0262436 A1 | 10/2008 | Olson |
| 2008/0269691 A1 | 10/2008 | Cowe |
| 2009/0005742 A1 | 1/2009 | Liversidge |
| 2009/0221972 A1 | 9/2009 | Gratwohl et al. |
| 2009/0254042 A1* | 10/2009 | Gratwohl et al. ............ 604/198 |
| 2009/0259178 A1 | 10/2009 | Brechbuehler et al. |
| 2009/0259196 A1 | 10/2009 | Gratwohl et al. |
| 2010/0114035 A1 | 5/2010 | Schubert et al. |
| 2010/0234811 A1 | 9/2010 | Schubert et al. |
| 2011/0022001 A1 | 1/2011 | Wei |
| 2011/0288491 A1 | 11/2011 | Newman et al. |

FOREIGN PATENT DOCUMENTS

| | | |
|---|---|---|
| DE | 102006022081 B3 | 1/2008 |
| DE | 10 2006 042 233 B3 | 3/2008 |
| DE | 102006041810 A1 | 3/2008 |
| EP | 1464353 A1 | 10/2004 |
| EP | 1747789 A2 | 1/2007 |
| EP | 1 949 926 A1 | 7/2008 |
| EP | 1 949 928 A1 | 7/2008 |
| FR | 2881053 A1 | 7/2006 |
| WO | 90/02515 A1 | 3/1990 |
| WO | 92/09319 A1 | 6/1992 |
| WO | 92/20281 A1 | 11/1992 |
| WO | 01/91837 A1 | 12/2001 |
| WO | 01/93924 A1 | 12/2001 |
| WO | 03/045480 A1 | 6/2003 |
| WO | 03/105935 A2 | 12/2003 |
| WO | 2004/000397 A1 | 12/2003 |
| WO | 2004030539 A1 | 4/2004 |
| WO | 2004/071560 A1 | 8/2004 |
| WO | 2005/097238 A2 | 10/2005 |
| WO | 2006018626 A1 | 2/2006 |
| WO | 2006/072807 A1 | 7/2006 |
| WO | 2007/077463 A1 | 7/2007 |
| WO | 2008/025179 A1 | 3/2008 |
| WO | 2008/028304 A1 | 3/2008 |
| WO | 2008/028305 A1 | 3/2008 |
| WO | 2008/028312 A1 | 3/2008 |
| WO | 2008/035122 A1 | 3/2008 |
| WO | 2008/043188 A1 | 4/2008 |
| WO | 2008/044067 A1 | 4/2008 |
| WO | 2008/050158 A2 | 5/2008 |
| WO | 2008/083037 A1 | 7/2008 |
| WO | 2009/003300 A1 | 1/2009 |
| WO | 2009/030056 A1 | 3/2009 |
| WO | 2009/114762 A1 | 9/2009 |
| WO | 2010/126432 A1 | 11/2010 |

* cited by examiner

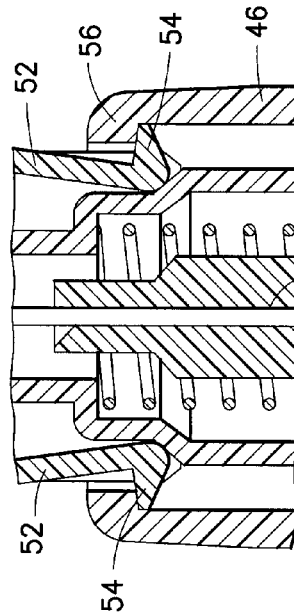
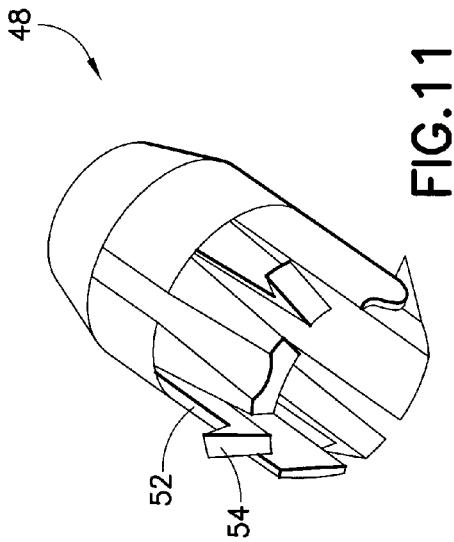
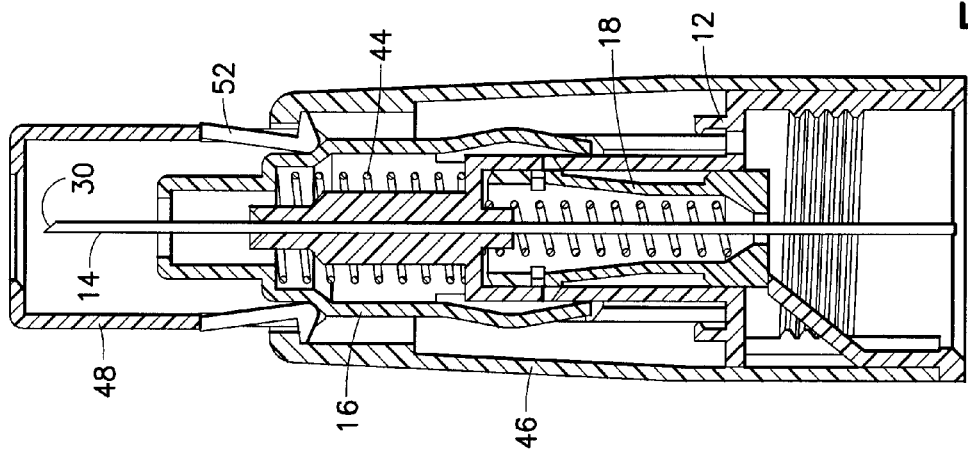

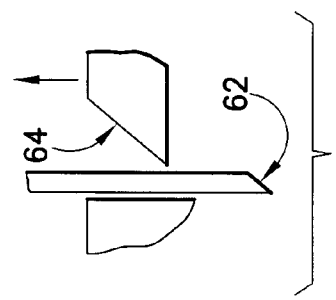
FIG.20
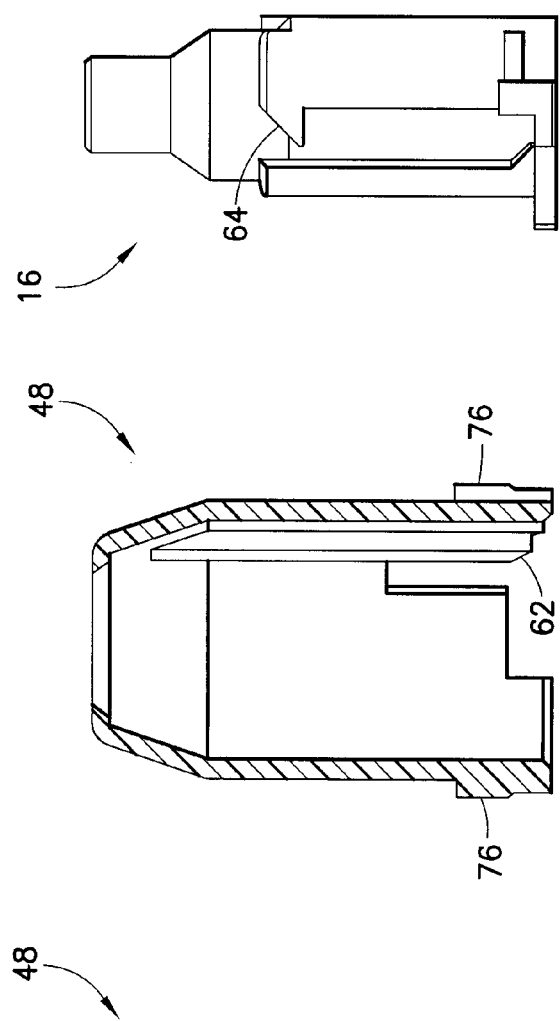
FIG.23
FIG.19
FIG.22
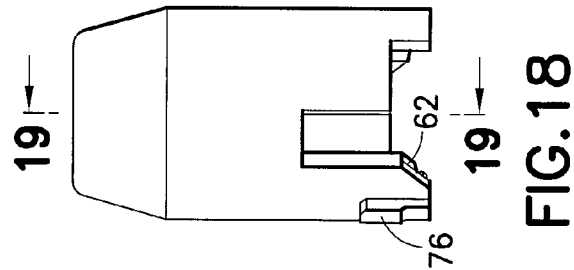
FIG.18
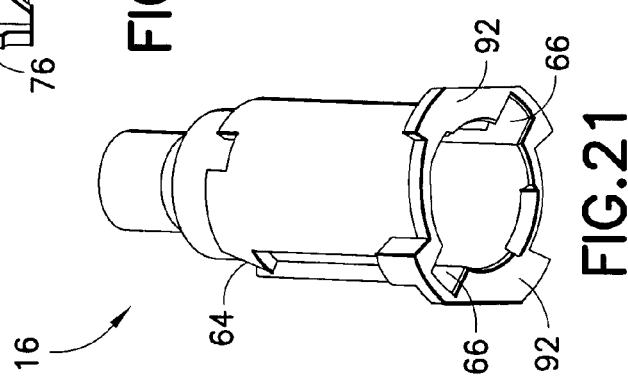
FIG.21

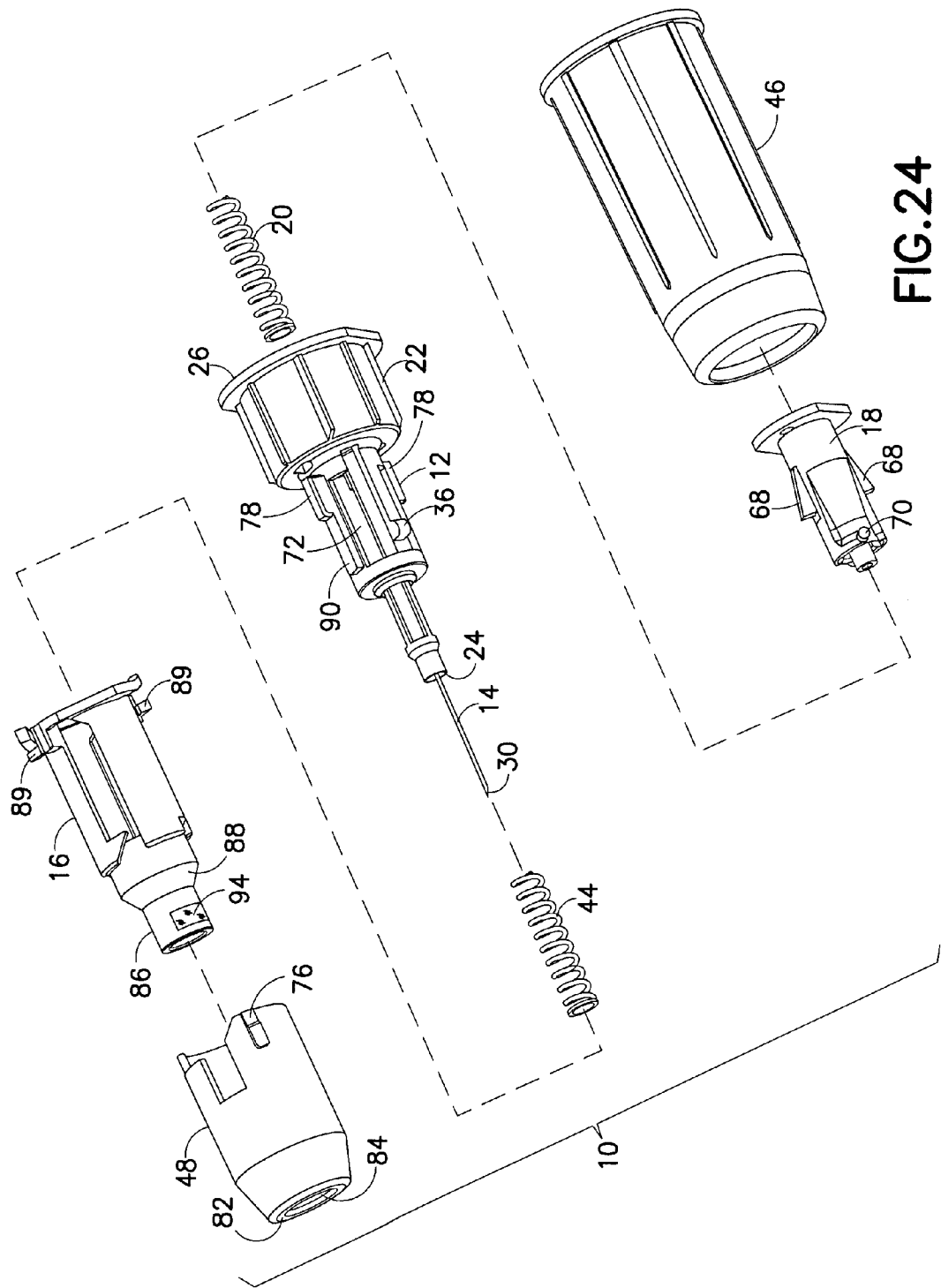

SAFETY PEN NEEDLE ASSEMBLY HAVING SHIELDING FOR PATIENT AND NON-PATIENT ENDS

CROSS-REFERENCES TO RELATED APPLICATIONS

This application is a continuation of U.S. application Ser. No. 12/922,802, filed on May 3, 2011, now allowed, which is a National Stage Application under 35 U.S.C. §371 of PCT/US2009/037084, filed on Mar. 13, 2009, which claims the benefit of priority to U.S. Provisional Application No. 61/036,138, filed on Mar. 13, 2008, which claims the benefit of priority to U.S. Provisional Application No. 61/036,299, filed on Mar. 13, 2008, which claims the benefit of priority to U.S. Provisional Application No. 61/055,686, filed on May 23, 2008, which claims the benefit of priority to U.S. Provisional Application No. 61/081,878, filed on Jul. 18, 2008, which claims the benefit of priority to U.S. Provisional Application No. 61/084,750, filed on Jul. 30, 2008, the entire contents of these applications being incorporated by reference herein.

BACKGROUND OF THE INVENTION

Pen injectors are known in the prior art and typically include a dose-adjustment mechanism for setting a dose, for example of insulin, and a pen needle for insertion into a patient to allow proper drug administration. The pen needle should be single-use and replaced with each administered dose.

The pen needle includes a distal end formed for insertion into a patient and a proximal end for insertion into a drug vial or cartridge located inside the pen injector. The proximal end of the needle will typically have to pierce a septum or stopper provided on the end of the vial or cartridge to access the drug. Devices have been developed in the prior art to shield the distal, or patient, end of the needle after use; particularly, to prevent an inadvertent "needle stick" after use. Even with the distal end being shielded, the proximal, or non-patient end, is exposed.

SUMMARY OF THE INVENTION

A safety pen needle assembly is provided herein which includes a hub and a needle fixed to the hub. Further, a first shield is provided, along with a second shield which has a biasing element disposed to urge the second shield proximally towards a proximal end of the needle. The assembly further includes a releasable retaining assembly for releasably retaining the second shield in an initial position against the force of the biasing element. A predetermined extent of movement of the first shield causes the retaining assembly to release the second shield, and, wherein, with the second shield being released, the second shield is urged proximally by the biasing element to a second position where the second shield covers the proximal end of the needle. Advantageously, with the subject invention, an assembly is provided which allows for passive activation of a shield on a non-patient end of a pen needle assembly by a patient-end shield.

These and other features of the invention will be better understood through a study of the following detailed description and accompanying drawings.

BRIEF DESCRIPTION OF THE DRAWINGS

FIGS. 6-23 show different arrangements useable with a third shield for activating the first shield with the subject invention; and, FIGS. 24-28 show a preferred embodiment of the subject invention.

DETAILED DESCRIPTION OF THE DRAWINGS

Figure 1:
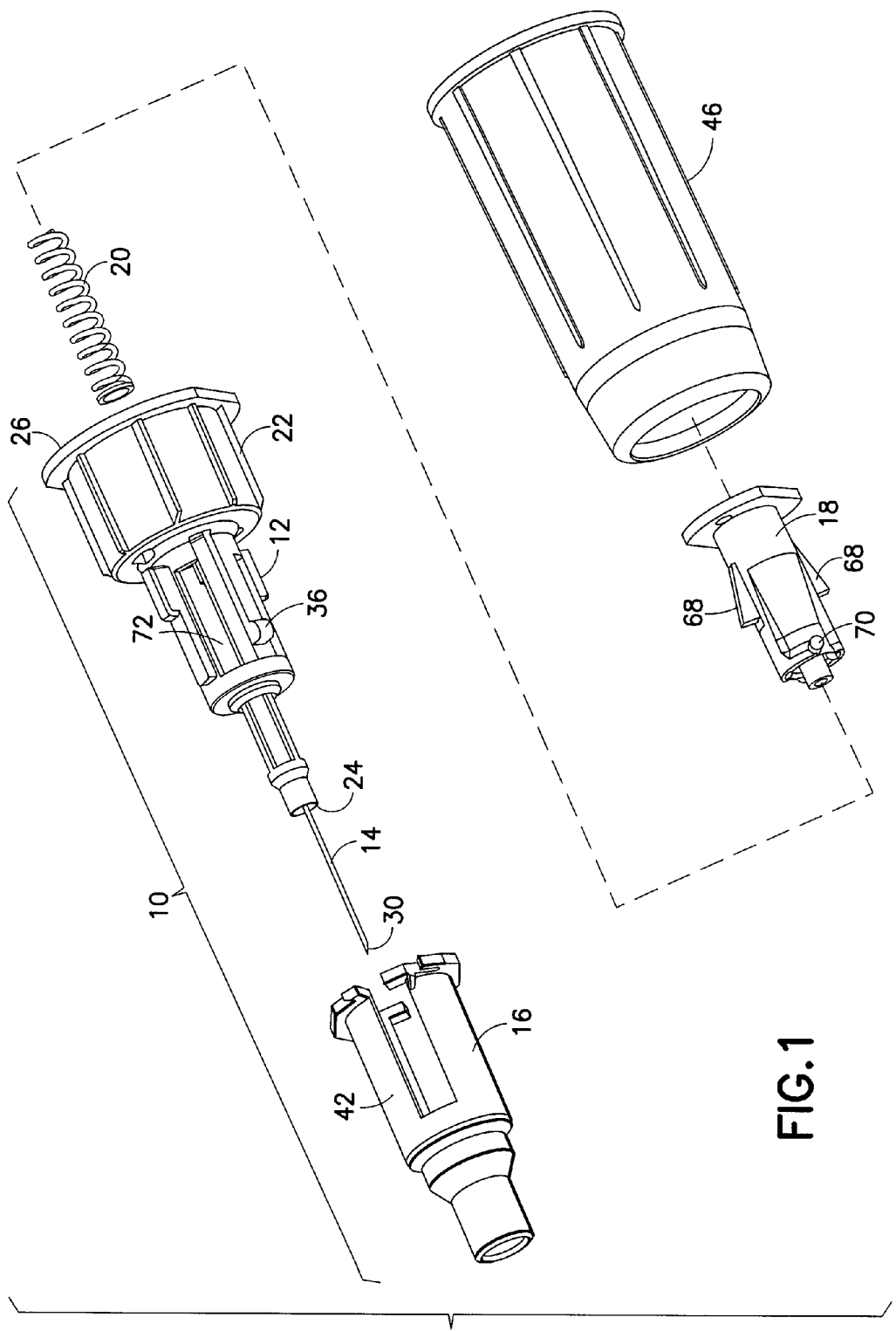
FIG. 1 is an exploded view of a safety pen needle assembly formed in accordance with the subject invention.

With reference to the figures, a safety pen needle assembly is shown and described herein which provides for shielding on a pen needle assembly, both on the patient (distal) and non-patient (proximal) ends. As used herein, the term "distal", and derivatives thereof, refer to the direction generally towards the patient end for use, and the term "proximal", and derivatives thereof, is used to describe the direction away from the patient during use.

With reference to FIGS. 1-4, a safety pen needle assembly is shown and generally designated with the reference number 10. The assembly 10 generally includes a hub 12, a needle 14 fixed to said hub 12, a first shield 16, a second shield 18, and a first biasing element 20.

The hub 12 includes a body 22 having a distal end 24 and a proximal end 26. The proximal end 26 is formed open and shaped to receive a portion of a pen injector body to allow the assembly 10 to be mounted onto a pen injector. Mounting features 28 may be formed on the hub 12 adjacent to the proximal end 26 formed to cooperate with mounting features provided on a pen injector. For example, the mounting features 28 may be threads or a surface configuration, such as a tapered surface for a luer-type mounting, or both.

The needle 14 may be of any needle design, particularly of any pen needle design. The needle 14 includes a distal end 30, formed for insertion into a patient, and a proximal end 32. As shown in the figures, the distal end 30 of the needle 14 extends distally beyond the distal end 24 of the hub 12. The proximal end 32 of the needle 14 may be within the interior of the hub 12 adjacent to the proximal end 26, or may extend proximally from the proximal end 26. The needle 14 may be fixed to the hub 12 using any known technique, such as being adherently fixed to the hub 12.

The first shield 16 is formed to at least partially encircle a portion of the needle 14. The hub 12 includes a transverse wall 34 located between the distal and proximal ends 24, 26 of the hub 12. The first shield 16 is located distally of the transverse wall 34. Preferably, the first shield 16 is moveable from an initial state where the distal end 30 of the needle 14 is exposed to a second state where the first shield 16 covers the distal end 30 of the needle 14.

The second shield 18 is also formed to at least partially encircle a portion of the needle 14. The second shield 18 is located proximally of the transverse wall 34. The second shield 18 is configured to move from a first state where the proximal end 32 of the needle 14 is exposed to a second state where the second shield 18 covers the proximal end 32 of the needle 14. The first biasing element 20 is disposed to urge the second shield proximally towards the proximal end 32 of the needle 14 so as to urge the second shield 18 from its first state to its second state. The first biasing element 20 may be located between a portion of the hub 12 and the second shield 18, such as between the transverse wall 34 and the second shield 18. The first biasing element 20 may be of any known design, including being a compression or coil spring.

Figure 2:
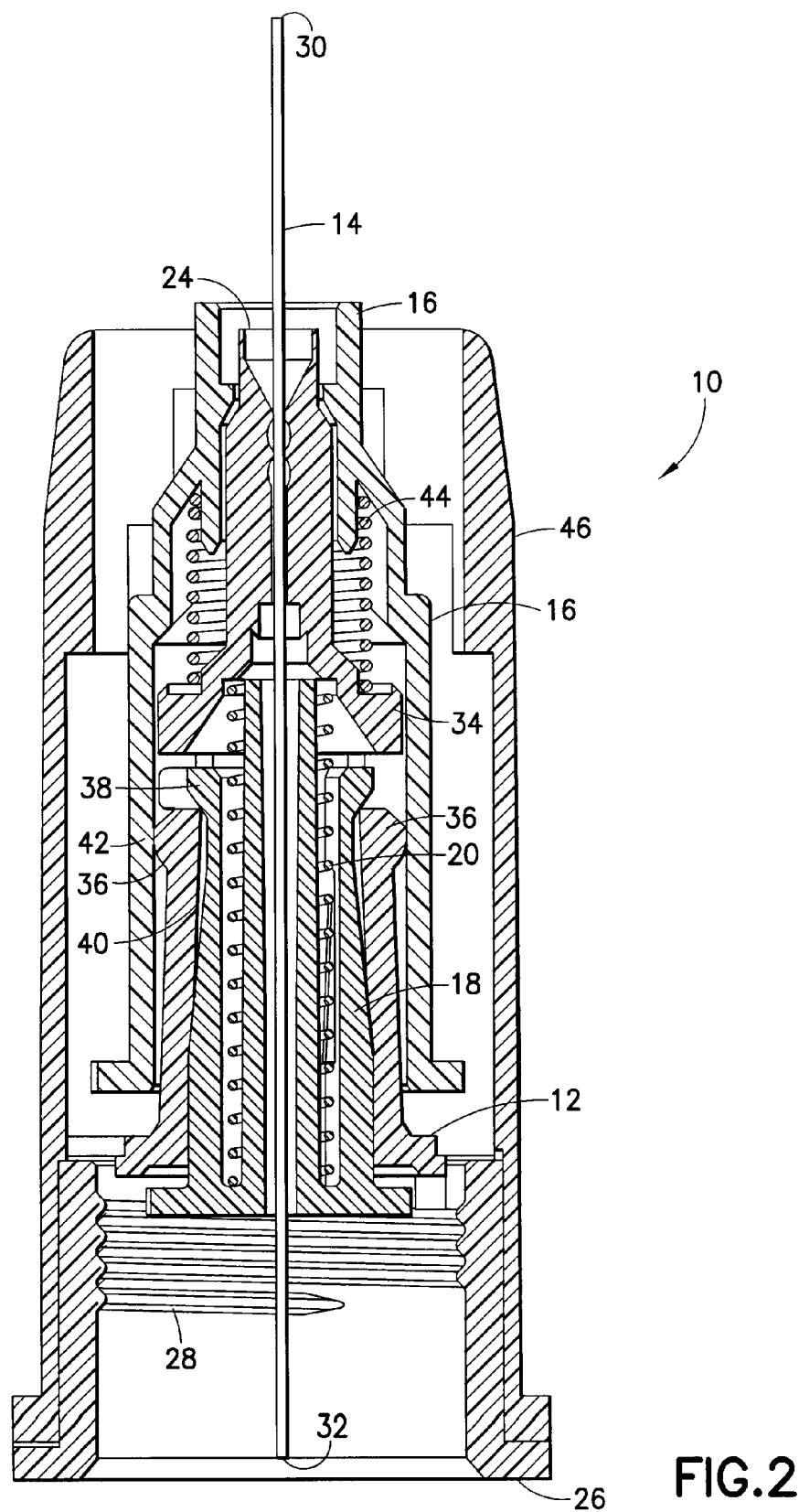
FIGS. 2-4 show the safety pen needle assembly of FIG. 1 in different states during use.

With reference to FIG. 2, the assembly 10 is shown in an initial state, with the proximal end 32 of the needle 14 being exposed. In addition, the second shield 18 is shown to be held in its first, initial state against the force of the first biasing element 20. The second shield 18 is retained in its first state by a releasable retaining arrangement. By way of non-limiting example, the releasable retaining arrangement may include one or more deflectable hub locking fingers 36 which are positioned to pressingly engage against the second shield 18, particularly in its first state. The hub locking fingers 36 are caused to deflect inwardly by the first shield 16, thus engaging the second shield 18. Preferably, a lip 38 is formed in the second shield 18. In the first state, the hub locking fingers 36 are positioned to pressingly engage against the lip 38, so as to resist proximal movement of the second shield 18. Frictional interengagement between the hub locking fingers 36 and the second shield 18 may enhance the ability of the hub locking fingers 36 to retain the second shield 18 in its initial state.

Figure 3:
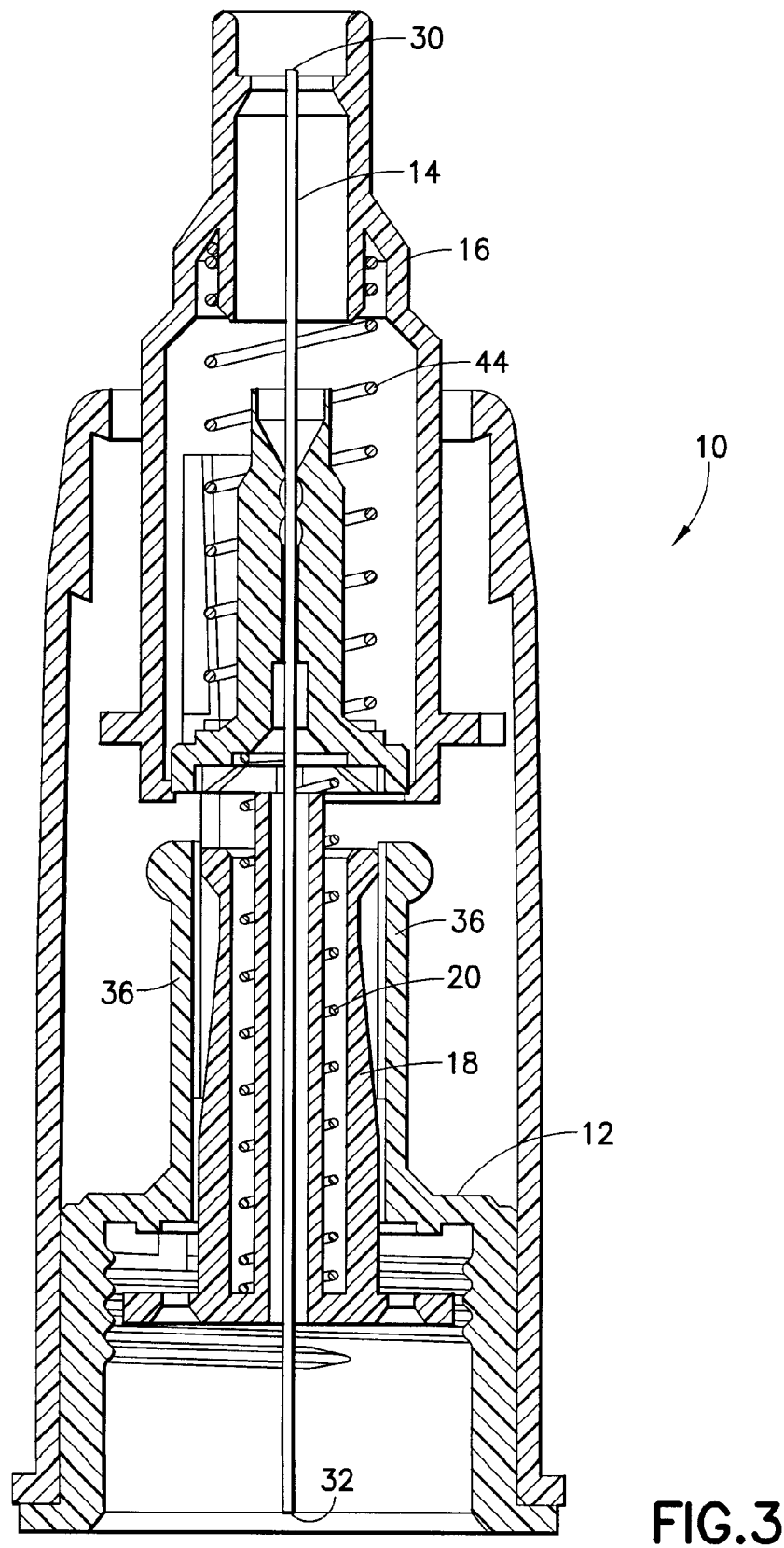
Figure 4:
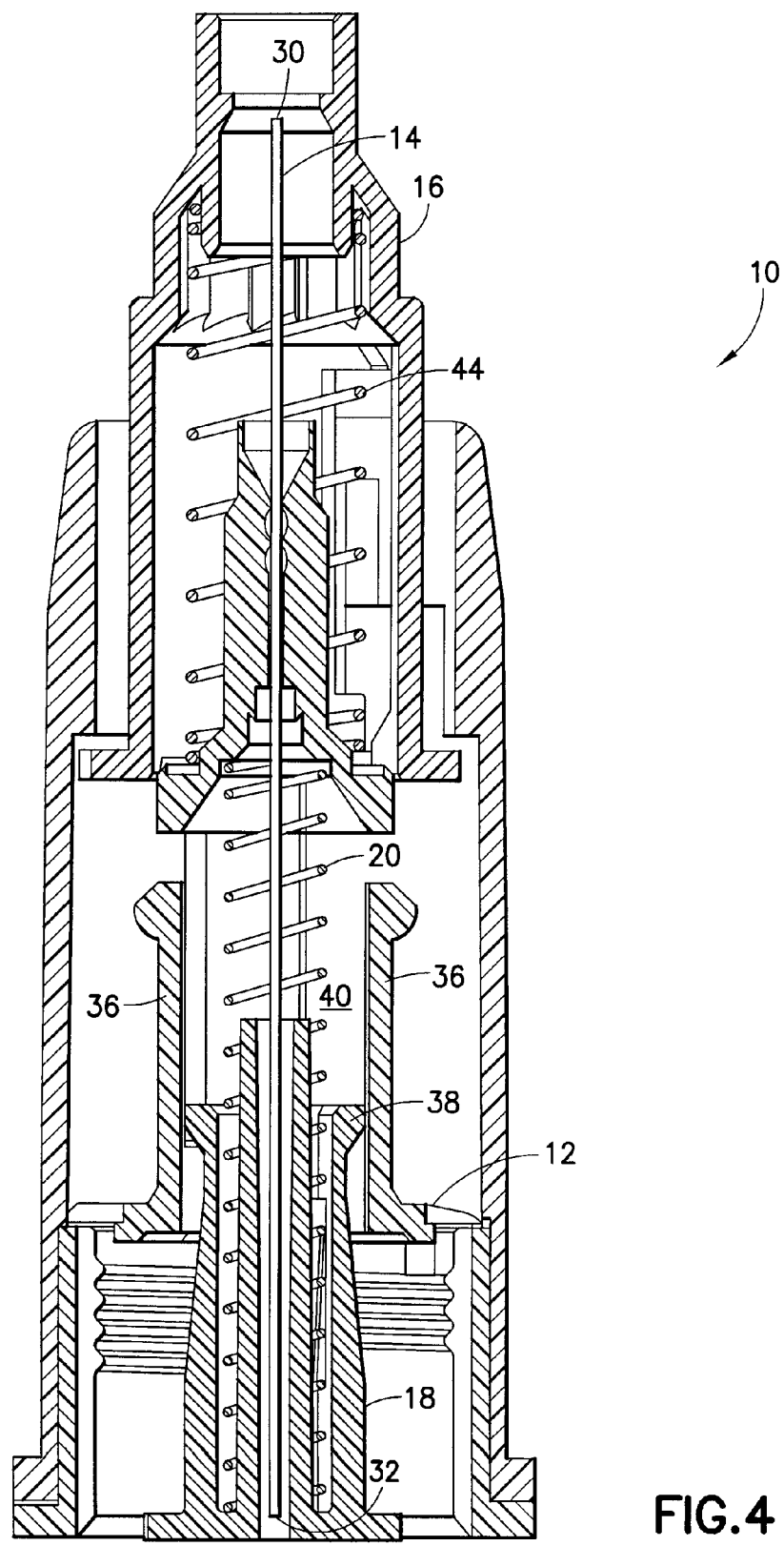

With reference to FIG. 3, with a predetermined extent of distal movement of the first shield 16 towards the distal end 30 of the needle 14, the first shield 16 disengages the hub locking fingers 36, thus allowing the hub locking fingers 36 to disengage from the second shield 18. As such, the second shield 18 may move proximally under force of the first biasing element 20 in a proximal direction towards the proximal end 32 of the needle 14. The second shield 18 is urged to its second state, where the proximal end 32 of the needle 14 is covered by the second shield 18, as shown in FIG. 4.

Figure 5:
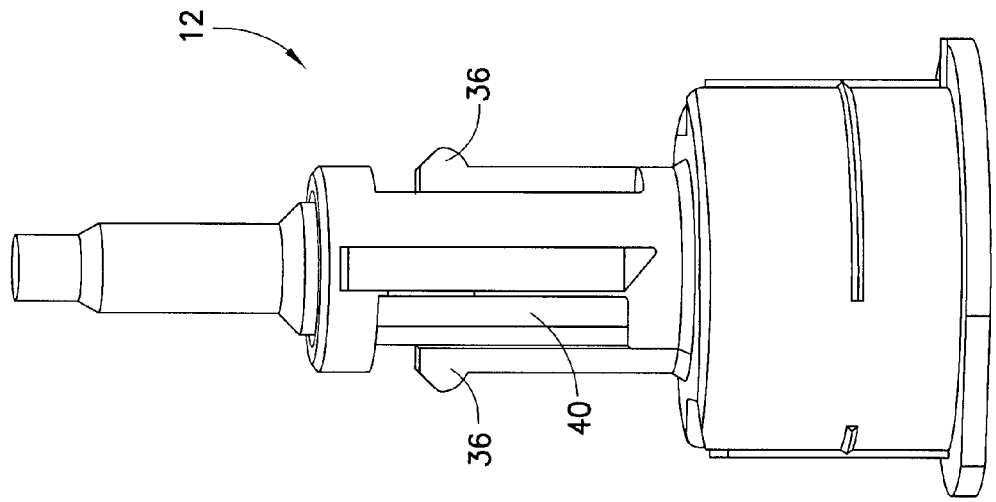
FIG. 5 shows a hub useable with the subject invention.

In a preferred arrangement, the hub 12 is formed with a channel 40 into which the second shield 18 is at least partially inserted. The hub locking fingers 36 are formed to deflect into the channel 40 in engaging the second shield 18. In natural, unbiased states, as shown in FIG. 5, the hub locking fingers 36 extend outwardly from the channel 40. In addition, an engagement portion 42 of the first shield 16 may be formed to telescope over the channel 40. Preferably, the inner diameter of the engagement portion 42 is selected so as to interferingly engage against the hub locking fingers 36 thus causing inward deflection thereof, particularly into the channel 40. With the distal movement of the first shield 16, the engagement portion 42 moves sufficiently distally so as to clear the hub locking fingers 36 thus allowing the hub locking fingers 36 to deflect outwardly, returning to its natural, unbiased state. As described above, this permits the second shield 18 to be urged proximally to its second state.

The first shield 16 may be urged distally by various ways, including being urged manually. Preferably, a second biasing element 44 (FIGS. 2 and 3) is provided disposed to urge the first shield 16 distally towards the distal end 30 of the needle 14. The second biasing element 44 may be located between a portion of the hub 12 and the first shield 16, such as being located between the transverse wall 34 and the first shield 16. Any retaining arrangement may be utilized to retain the first shield 16 in its initial state, with the distal end 30 of the needle 14 being exposed. The first shield 16 may be passively or actively activated to move distally, thus allowing the second shield 18 to move proximally.

As shown in FIGS. 1-4, an outer sleeve 46 may be provided which is part of the hub 12. The outer sleeve 46 may be formed unitarily with the body 22 or affixed thereto.

In a preferred arrangement, and with reference to FIGS. 6-23, the first shield 16 is caused to be activated by a third shield 48. The first shield 16 may be activated by releasing from a releasable retaining arrangement which retains the first shield 16 in an initial, pre-use state, the initial pre-use state being shown in FIG. 2. The first shield 16 may be retained by a movable element formed on the hub 12, the element being displaceable by a predetermined extent of proximal movement of the third shield 48. Alternatively, the third shield 48 may have movable elements for releasably retaining the first shield 16, such as deflectable locking arms. Further, the first and third shields 16, 48 may have cooperating elements for causing relative movement therebetween and release thereof.

Figure 6:
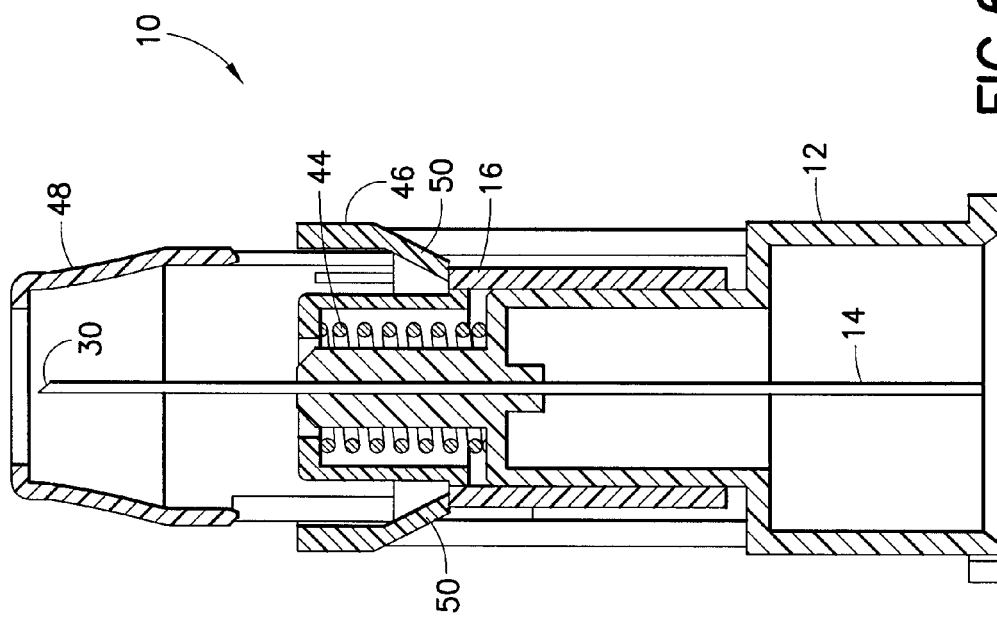
Figure 8:
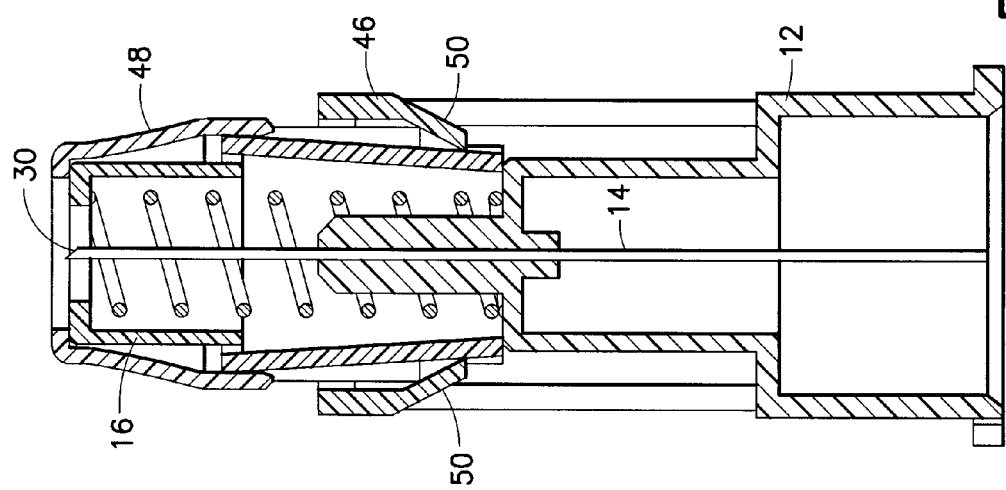
Figure 7:
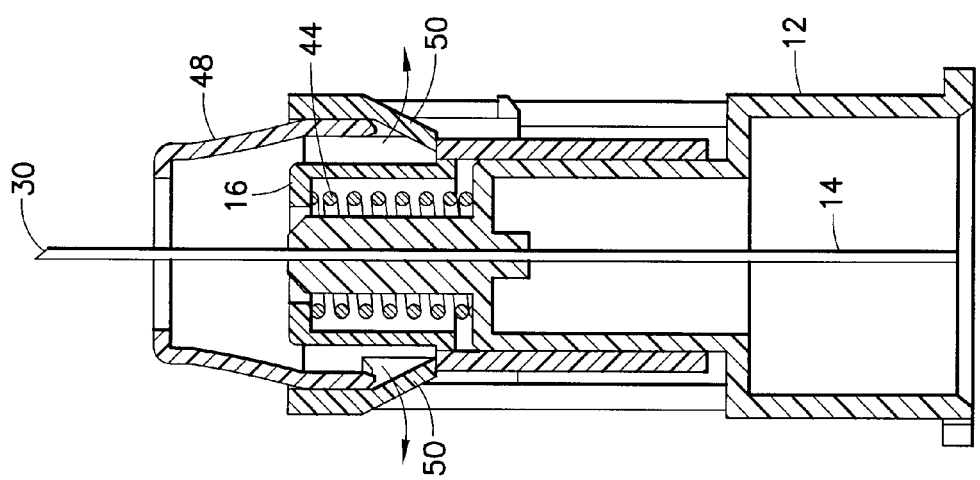

With reference to FIGS. 6-8, the hub 12, particularly at the sleeve 46, may be formed with one or more adjustable tabs 50 formed to extend inwardly to interferingly engage the first shield 16 and resist distal movement thereof against the force of the second biasing element 44. As shown in FIGS. 7-8, with sufficient proximal movement of the third shield 48, the tabs 50 are adjusted outwardly thus coming out of engagement with the first shield 16. This releases the first shield 16 which moves distally under the force of the second biasing element 44 to a shielding position covering the distal end 30 of the needle 14.

With reference to FIGS. 9-17, an alternative releasable retaining configuration is provided for releasably retaining the first shield 16 in the state shown in FIG. 9. The releasable retaining configuration may be provided with the third shield 48 having formed thereon at least one inwardly deflectable retaining arm 52. In an initial, before use state, the one or more retaining arms 52 are inwardly deflected, as shown in FIG. 9, to interferingly engage the first shield 16 so as to prevent distal movement of the first shield 16 under force of movement of the second biasing element 44. The inward deflection of the retaining arms 52 may be caused by engagement with the surrounding portion of the hub 12, particularly at the sleeve 46. The hub 12 may be configured (e.g., radially sized) to cause the inward deflection of the retaining arms 52. Optionally, the retaining arm(s) 52 may each be provided with a hook 54 for engaging inwardly-extending lip 56 formed on the hub 12 (FIGS. 10 and 11). The interengagement of the hooks 54 and the lip 56 prevents the first shield 16 from coming out of the hub 12 before use under force from the second biasing element 44.

Figure 12:
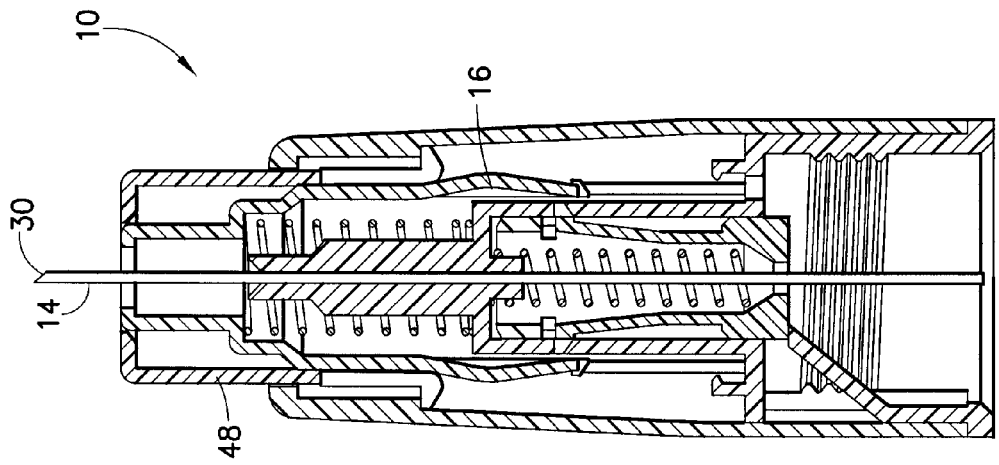

With reference to FIGS. 12-17, use of the safety pen needle assembly 10 is shown. FIG. 12 shows the third shield 48 having been moved proximally from the initial, before use state shown in FIG. 9. Proximal movement is achieved with the third shield 48 being pressed against a patient's skin and further pressure being applied causing the third shield 48 to move proximally relative to the rest of the safety pen needle assembly 10.

Figure 13:
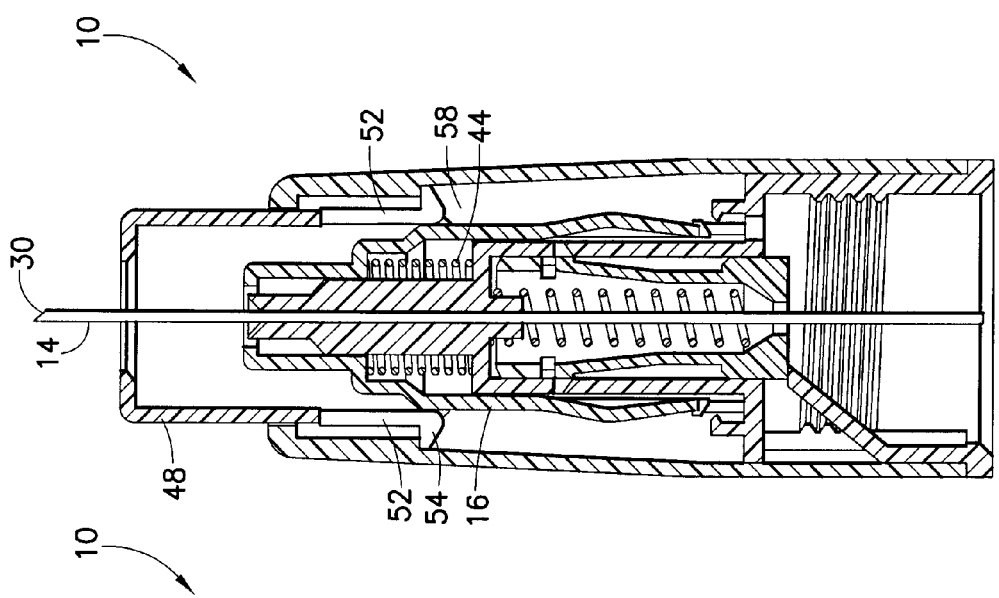
Figure 14:
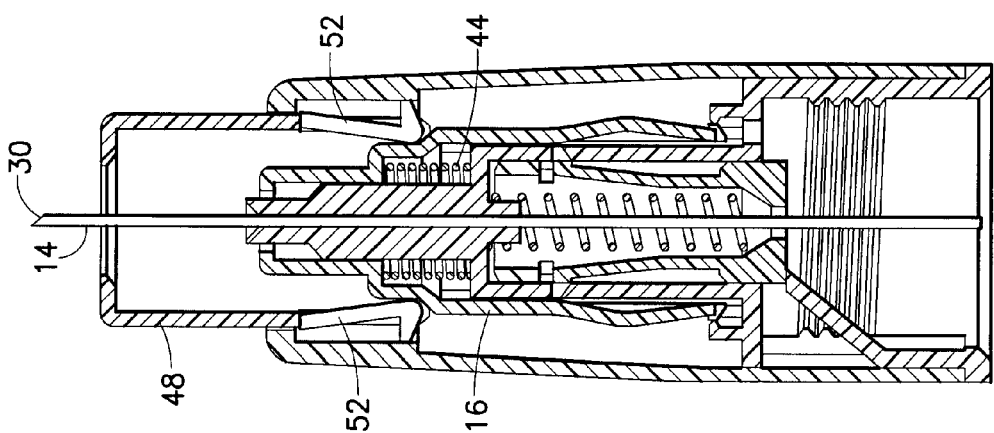
Figure 17:
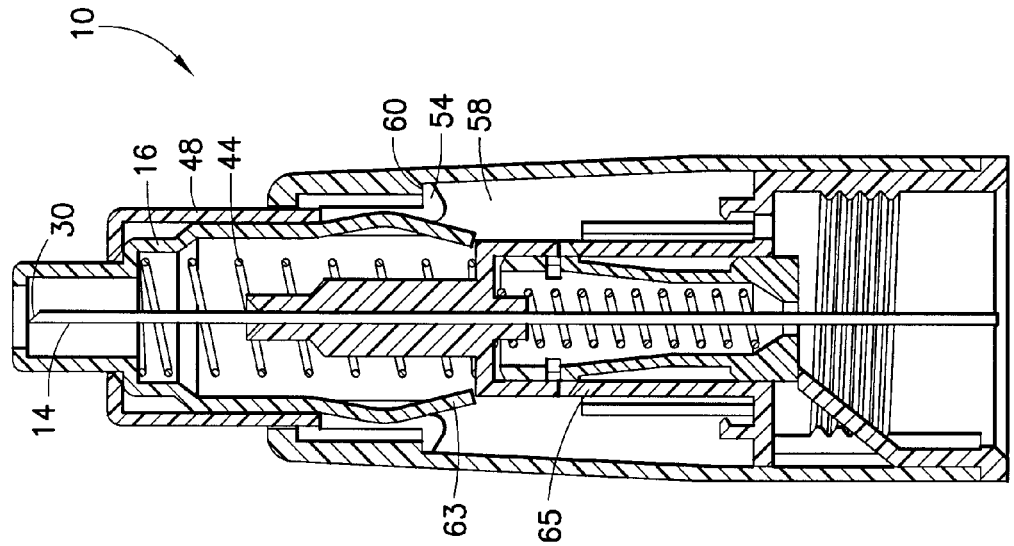
Figure 16:
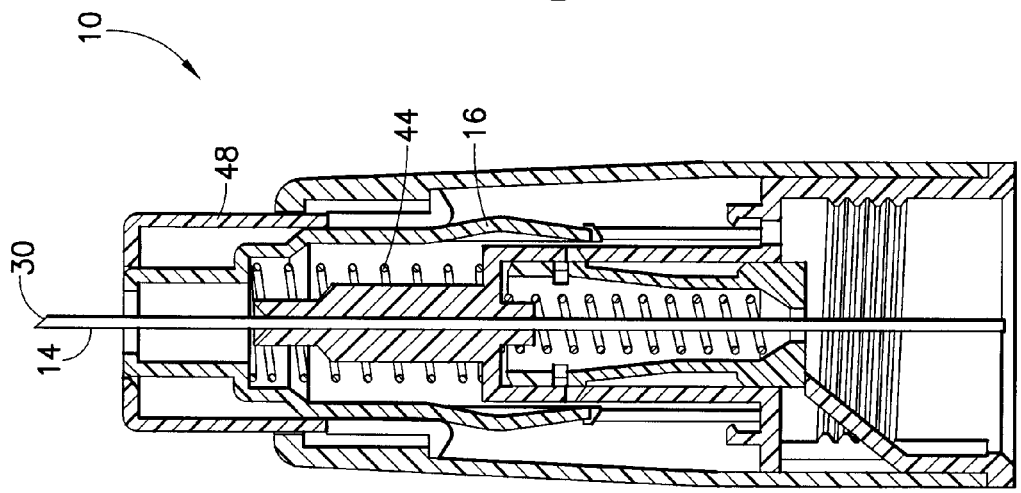
Figure 15:
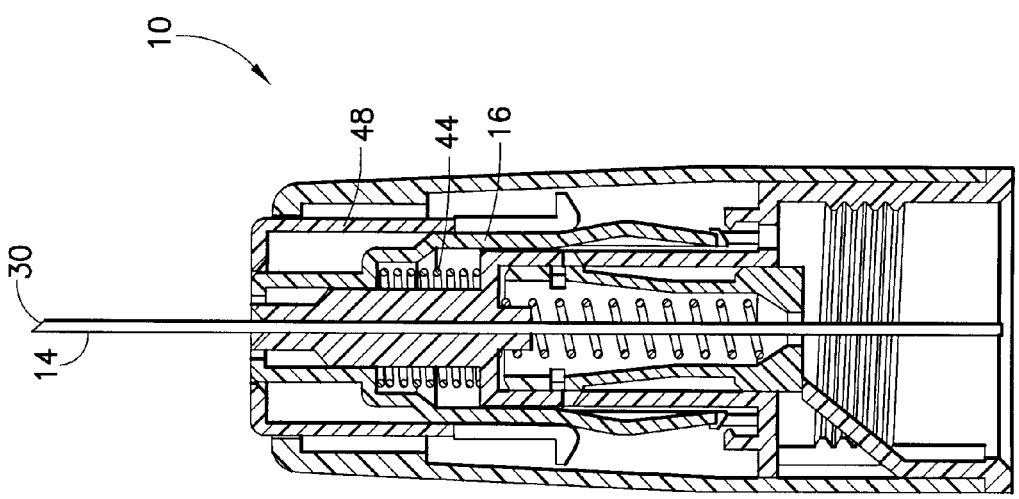

In the state shown in FIG. 12, the one or more retaining arms 52 still interferingly engage the first shield 16. With sufficient extent of proximal movement of the third shield 48, as shown in FIG. 13, the retaining arms 52 deflect outwardly to no longer prevent distal movement of the first shield 16. Enlarged area 58 may be provided in the hub 12 for permitting the retaining arms 52 to deflect outwardly, particularly the hooks 54. With no interference from the retaining arms 52, and with reference to FIG. 14, the second biasing element 44 causes the first shield 16 to move distally. The first shield 16 moves to the state shown in FIG. 14 where the first shield 16 and the third shield 48 are pressed against a patient's skin. As shown in FIG. 15, with further pressure applied to the safety pen needle assembly 10, the first and third shields 16, 48 are urged further proximally to expose the needle 14 in conducting a full injection. With reference to FIGS. 16 and 17, after the injection and as the needle 14 is withdrawn from a patient, the second biasing element 44 causes the first shield 16 to move distally. The first shield 16 moves to a shielding position where the distal end 30 of the needle 14 is covered.

As shown in FIG. 17, the interengagement between the third shield 48 and the first shield 16 limits distal movement of the first shield 16. Further, a ridge 60 may be defined within the hub 12 (e.g. adjacent to the enlarged area 58) disposed to be engaged by the hooks 54 in a final after-use state (FIG. 17).

The ridge 60 is distally spaced from the lip 56. The interengagement of the hooks 54 with the ridge 60 limits the distal movement of the third shield 48. This limited extent of distal movement of the third shield 48, in turn, causes limited distal movement of the first shield 16.

A locking arrangement may also be provided to limit proximal movement of the first shield 16 once in the final shielding position where the first shield 16 covers the distal end 30 of the needle 14. To this end, and with reference to FIG. 17, the first shield 16 may be provided with at least one inwardly deflectable locking arm 63 which is formed to be biased against a sleeve portion 65 of the hub 12 prior to the final shielding position of the first shield 16. The sleeve portion 65 may be defined about the channel 40. Upon sufficient distal movement of the first shield 16, as shown in FIG. 17, the locking arms 61 move clear of the sleeve portion 63 thereby permitting the locking arms 63 to deflect radially inwardly. The locking arms 63, deflected inwardly, interferingly engage a portion of the hub 12, particularly above the sleeve portion 65, so as to prevent proximal movement of the first shield 16. The locking arms 63 may also be formed to be curved or bent outwardly so as to engage the second shield 20 as the first shield 18 initially moves distally, as shown in FIGS. 15 and 16. This permits movement of the third shield 48 in concert with movement of the first shield 16. The curved or bent locking arms 63 are deflected inwardly as the first shield 16 slides inside of the third shield 48 by the engagement with the third shield 48. When the locking arms 63 move clear of the sleeve portion 65, the locking arms 63 deflect radially inwardly. The locking arms 63, deflected inwardly, interferingly engage a portion of the hub 12, particularly above the sleeve portion 65, so as to prevent proximal movement of the first shield 16 as shown in FIG. 17.

As a further variation, the releasable retaining arrangement may be defined by cooperating elements on the first and third shields 16 and 48 which cause relative movement between the first shield 16 and the third shield 48 with the first shield 16 being released. For example, with reference to FIGS. 18-23, the third shield 48 may cause relative movement (e.g., rotation) between the first shield 16 and the third shield 48 so as to allow the first shield 16 to move from a retained position to a second, free position where the first shield 16 may be urged distally.

By way of non-limiting example, and specifically, with reference to FIGS. 18 and 19, the third shield 48 may include a protruding tapered surface 62. As shown in the figures, the tapered surface 62 may extend inwardly of the third shield 48, but may also extend outwardly. Correspondingly, a tapered receiving surface 64 may be formed on the first shield 16. The first and third shields 16, 48 are configured so that with the third shield 48 telescoped over the first shield 16, the tapered surface 62 will axially engage in abutting contact the receiving surface 64. Thus, in an initial state, the tapered surface 62 is aligned with the receiving surface 64. This interengagement retains the first shield 16 in an initial position against force of the second biasing element 44.

With proximal movement of the third shield 48 relative to the first shield 16, relative rotation between the first and third shields 16, 48 may be generated due to the tapered surfaces 62, 64 against each other under proximal movement. Preferably, the first shield 16 is non-rotatably held during the proximal movement of the third shield 48. With reference to FIG. 21, one or more lobes 66 may be formed on the first shield 16 for receiving portions of the hub 12. This interengagement limits rotation of the first shield 16 relative to the hub 12. With the first shield 16 being held in a fixed radial position, as shown in FIGS. 22 and 23, the tapered surface 62 is caused to rotate out of engagement with the receiving surface 64. Once the receiving surface 64 is clear, the first shield 16 may be driven distally by the second biasing element 44. As will be appreciated by those skilled in the art, the first shield 16 may be caused to move relatively to the third shield 48, vice versa, or the first and third shields 16, 48 may be both caused to move relatively. The relative movement may cause the first shield 16 to be freed of any retaining element, such element being formed in the third shield 48 and/or elsewhere (e.g., on the hub 12).

As will be appreciated by those skilled in the art, various releasable retaining arrangements are described above. It is to be understood that these arrangements may be used in various combinations and with any of the various embodiments. The releasable retaining arrangement may be defined by one or more movable elements defined on the hub; one or more movable elements defined on one of the shields (e.g., the second shield); and/or an arrangement defined between the shields wherein relative movement (e.g., radial movement) allows for release of the relevant shield.

It is further preferred that the assembly 10 be provided with a locking arrangement to the lock the second shield 18 in the shielding position. With reference to FIG. 1, the second shield 18 may be provided with one or more deflectable locking arms 68, having a natural, unbiased state as shown in FIG. 1. In this state, the locking arms 68 define a larger diameter than the channel 40 defined in the hub 12. With the second shield 18 being urged proximally, the second shield 18 is urged sufficiently to have the locking arms clear the channel 40. Inside of the channel 40, the locking arms 68 are deflected inwardly. As shown in FIG. 4, with the locking arms 68 clearing the channel 40, the locking arms 68 return to the unbiased state. With a larger diameter, the locking arms 68 prevent distal movement of the second shield 18. In addition, one or more protrusions 70 may extend from the second shield 18 formed to slide along guide channels 72 formed in the hub 12, particularly about the channel 40. The interengagement between the protrusions 70 and the guide channels 72, particularly at the proximal ends of the guide channels 72, limits proximal movement of the second shield 18. Taking the restriction on both proximal and distal movement of the second shield 18, the second shield 18 is locked in position.

Preferred Embodiment

With reference to FIGS. 24-28, a preferred embodiment of the safety pen needle assembly 10 is depicted. With specific reference to FIG. 24, the preferred embodiment of the safety pen needle assembly 10 includes all the components described above with respect to FIG. 1 and further includes the use of the second biasing element 44 and the third shield 48. In the preferred embodiment, the first shield 16 and the third shield 48 are configured as shown in FIGS. 18-21.

Figure 25:
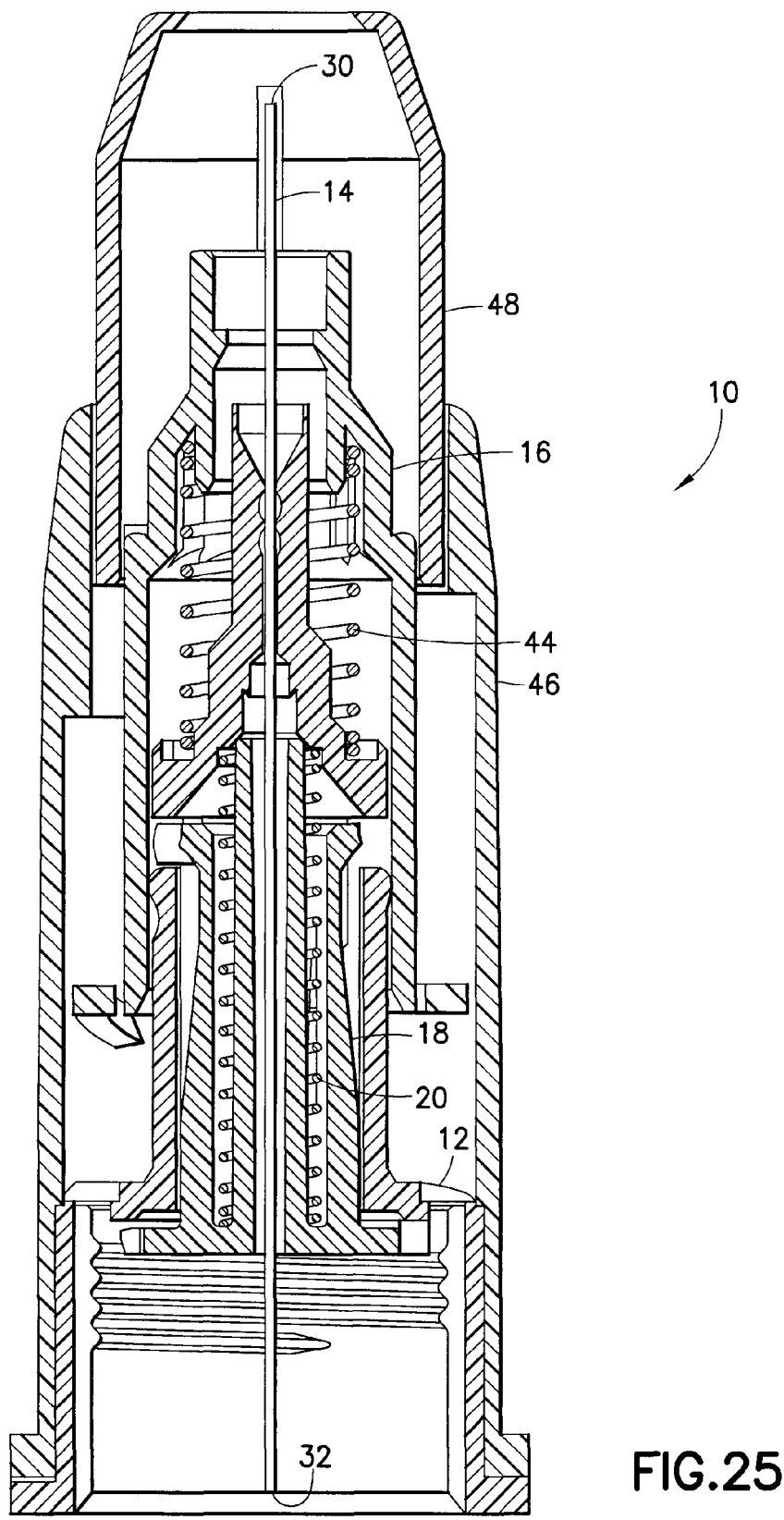
Figure 26:
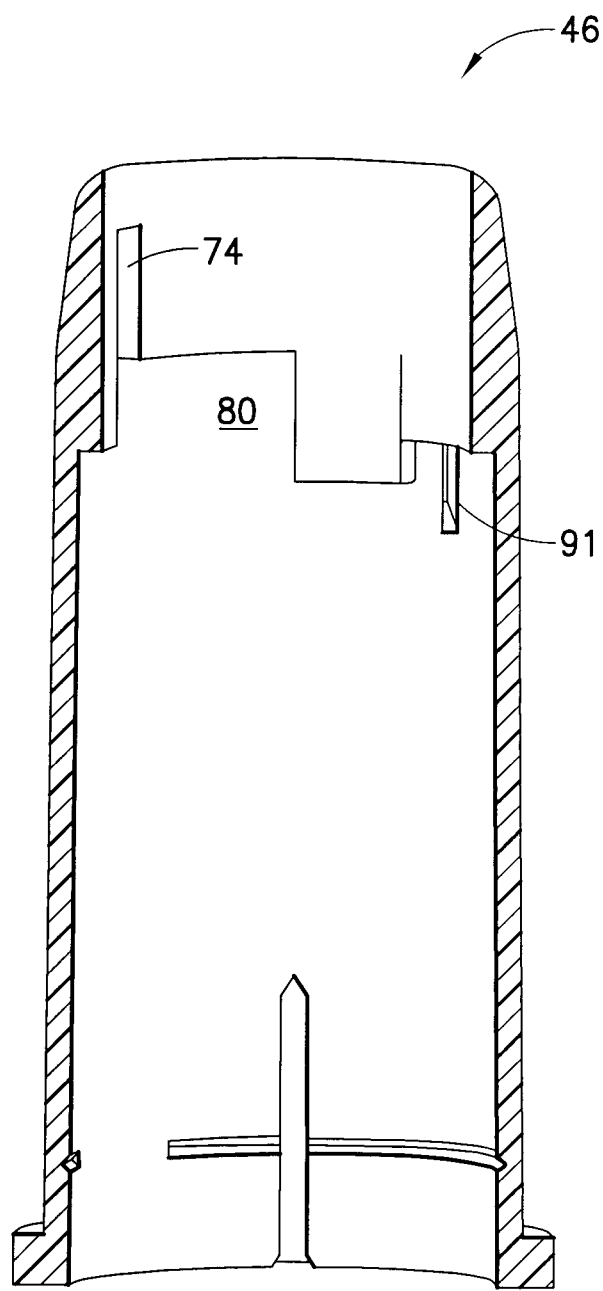

With reference to FIG. 25, the preferred embodiment of the safety pen needle assembly 10 is shown in an initial, pre-use state. In this state, the third shield 48 retains the first shield 16 in the initial state against the force of the second biasing element 44. With reference to FIG. 26, the outer sleeve 46 is internally formed with one or more grooves 74 formed to receive detents 76 (FIGS. 18, 19 and 24) formed on the third shield 48. In an initial state, in the manner described with respect to FIGS. 18-23, the tapered surface 62 on the third shield 48 is aligned with the receiving surface 64 formed on the first shield 16. In addition, ears 78 are formed on the hub 12 which nest in the lobes 66 of the first shield 16. With this arrangement, the detents 76 are nested in the grooves 74 formed in the outer sleeve 46, which, thus, prevents rotation of the third shield 48 relative to the remainder of the assembly 10. In addition, the interengagement of the lobes 66 and the ears 78 prevents relative rotation of the first shield 16 relative to the remainder of the assembly 10.

In the initial state, the second biasing element 44 applies biasing force to the first shield 16 which, in turn, transmits the biasing force to the third shield 48 via the engagement between the tapered surface 62 and the receiving surface 64. The detents 76 engage the ends of the grooves 74 so as to limit the extent of distal movement of the third shield 48. In this manner, the first shield 16 is retained in the initial state.

During use, the third shield 48 is caused to move proximally. Due to the nesting of the detents 76 and the grooves 74, the third shield 48 is only permitted to move axially, without rotation. Upon a sufficient amount of proximal movement, the detents 76 clear the grooves 74 and enter into clearance areas 80, shown in FIG. 26. Due to the tapered nature of the tapered surface 62 and the receiving surface 64, as described above with respect to FIGS. 18-23, the third shield 48 is caused to rotate with the detents entering into the clearance areas 80. Simultaneously, the tapered surface 62 come out of engagement with the receiving surface 64, thus allowing the first shield 16 to be urged distally under force of the second biasing element 44.

Figure 27:
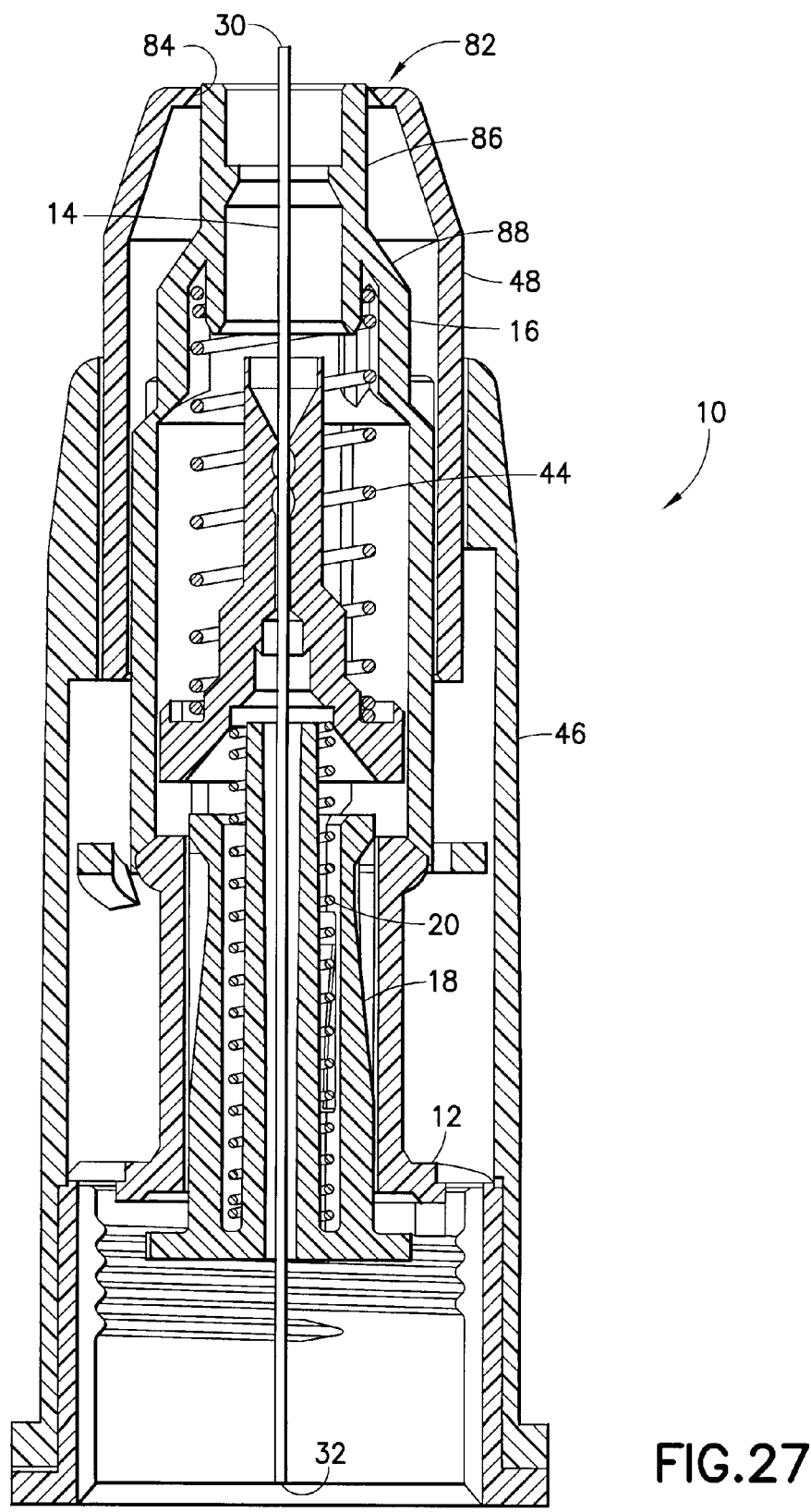

With reference to FIG. 27, during use, the third shield 48 is urged proximally due to distal end 82 of the third shield 48 being pressed against a patient's skin. An opening 84 is formed in the distal end 82. Preferably, the first shield 16 includes a reduced-diameter portion 86 at its distal end which is sized to pass through the opening 84. A shoulder 88 formed on the first shield 16 limits the extent of passage of the first shield 16 through the opening 84. As shown in FIG. 27, the first shield 16 is driven under force of the second biasing element 44 into the opening 84 so as to also be pressed against a patient's skin. The patient's skin restricts further distal movement. Sufficient distal movement of the first shield 16 allows for release of the second shield 18 in the manner described above. With the assembly 10 being mounted onto an injector, the injector will prevent the second shield 18 from fully shielding the proximal end 32 of the needle 14.

Figure 28:
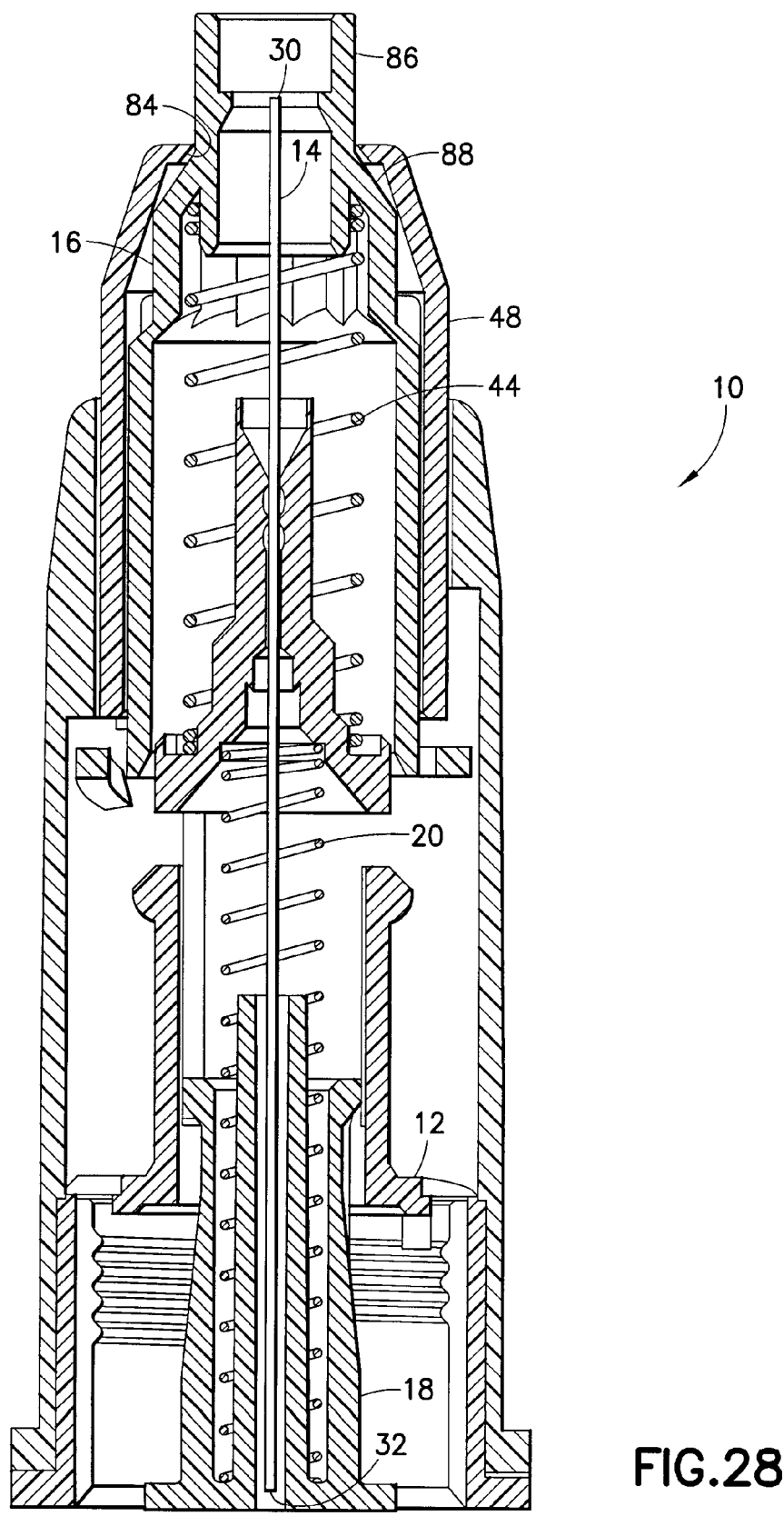

After completion of the injection, the needle 14 is withdrawn from a patient and the first shield 16 is allowed to be urged further distally by the second biasing element 44 to a shielding position as shown in FIG. 28, where the first shield 16 covers the distal end 30 of the needle 14. The interengagement of the shoulder 88 and the opening 84 limits the extent of distal movement of the first shield 16.

It is also preferred that the first shield 16 be locked in the shielding position. With reference to FIG. 24, it is preferred that the hub 12 be provided with ridges 90 which extend from the ears 78. The ridges 90 and the ears 78 may be formed with one continuous height without interruption. As the first shield 16 is urged distally, the lobes 66 translate across the ridges 90. With the first shield 16 clearing the ridges 90, particularly at the lobes 66, it is preferred that the first shield 16 be forced to rotate so that the lobes 66 come out of alignment with the ridges 90. The second biasing element 44 may be provided with a torsional component, such as being pre-biased with a torsional force to cause such rotation upon the first shield 16 clearing the ridges 90. As shown in FIG. 21, the first shield 16 is formed with solid portions 92 adjacent to the lobes 66. The first shield 16 is rotated so that the solid portions 92 align with the ridges 90 and, thus, prevent proximal movement of the first shield 16. As will be appreciated by those skilled in the art, any mechanism for limiting reverse rotation against the force of the second biasing element 44 may be utilized. By way of non-limiting example, one or more flexible fingers 89 may extend out from the first shield 16. The flexible fingers 89 extend in the same intended direction of rotation applied to achieve locking. With reference to FIG. 26, one or more corresponding locking ridges 91 are formed on the interior of the outer sleeve 46 such that with rotation of the first shield 16 to its locking position, the flexible fingers 89 snap past the corresponding locking ridges 91. Inherent resilience of the flexible fingers 89 allows for the snap engagement. The interengagement between the flexible fingers 89 and the locking ridges 91 prevents reverse rotation of the first shield 16 and maintains the lobes 66 out of alignment with the ridges 90 (i.e., the locked state of the first shield 16 is maintained).

With removal of the assembly 10 from the injector, the second shield 18 is allowed to move proximally and travel to the shielding state shown in FIG. 28.

It is also preferred that that first shield 16, particularly at the reduced diameter portion 88 be provided with a visual indicator area 94 for indicating post-use. The visual indicator area 94 may be a colored and/or textured area which is distinguishable from surrounding portions of the first shield 16. With the first shield 16 being nested in the outer sleeve 46 during use, the visual indicator area 94 is obstructed from view. After use, the visual indicator area 94 becomes visible. The visual indicator area 94 provides a user with a simple manner of identifying whether the assembly 10 has been used. The visual indicator area 94 may be a region or band (e.g., continuous about the reduced diameter portion 88) which is colored and/or textured. Wording (such as "CAUTION-BIOHAZARD") and/or symbols and/or graphics may also be utilized.

What is claimed is:

1. A safety pen needle assembly comprising:
   a hub having at least one resilient hub locking finger;
   a needle fixed to said hub, said needle having a distal end, formed for insertion into a patient, and a proximal end;
   a first shield having a tubular body at least partially encircling a portion of said needle;
   a second shield having a lip and a tubular body at least partially encircling a portion of said needle; and,
   a first biasing means disposed to urge said second shield from an initial state, in which said second shield does not cover said proximal end of said needle, proximally towards said proximal end of said needle,
   wherein, with said second shield in said initial state, said first shield engaging said at least one resilient hub locking finger so as to deflect said at least one resilient hub locking finger radially inwardly into pressing engagement with said lip on said second shield to retain said second shield in said initial state,
   wherein, a predetermined extent of distal movement of said first shield towards said distal end of said needle causes said first shield to come out of engagement with said at least one resilient hub locking finger thus allowing said at least one resilient hub locking finger to release said lip of said second shield, and,
   wherein, with said second shield being released, said second shield is urged proximally by said first biasing means to a second position where said second shield covers said proximal end of said needle.

2. An assembly as in claim 1, further comprising a second biasing means disposed to urge said first shield distally towards said distal end of said needle.

3. An assembly as in claim 1, further comprising a third shield, said third shield having a tubular body at least partially encircling a portion of said needle.

4. An assembly as in claim 3, further comprising a second biasing means disposed to urge said first shield distally towards said distal end of said needle.

5. An assembly as in claim 4, wherein secondary releasable retaining means are provided for releasably retaining said first shield in an initial position against the force of said second biasing means.

6. An assembly as in claim 5, wherein, a secondary predetermined extent of movement of said third shield causes said secondary retaining means to release said first shield.

7. An assembly as in claim 6, wherein, upon release from said secondary retaining means, said first shield traverses said predetermined extent of distal movement under force of said second biasing means thereby causing said second shield to be released.

8. An assembly as in claim 7, wherein, upon release from said secondary retaining means, said first shield is urged distally under force of said second biasing means to a second position where said first shield covers said distal end of said needle.

9. An assembly as in claim 6, wherein, upon release from said secondary retaining means, said first shield is urged distally under force of said second biasing means to a second position where said first shield covers said distal end of said needle.

* * * * *